United States Patent

Lindgren

[11] 4,054,491
[45] Oct. 18, 1977

[54] MICROORGANISM TESTING DEVICE AND METHOD

[75] Inventor: Sven E. Lindgren, Uppsala, Sweden

[73] Assignee: Kemanord AB, Stockholm, Sweden

[21] Appl. No.: 523,376

[22] Filed: Nov. 13, 1974

[30] Foreign Application Priority Data

Nov. 13, 1973 Sweden .......................... 7315344

[51] Int. Cl.² ........................................ C12K 1/04
[52] U.S. Cl. ............................ 195/103.5 M; 195/139
[58] Field of Search ............... 195/103.5 R, 127, 139, 195/103.5 M; 23/259 R; 128/2 F, 234 R

[56] References Cited

U.S. PATENT DOCUMENTS

| 1,231,772 | 7/1917 | Meyer | 128/234 |
|---|---|---|---|
| 1,540,215 | 6/1925 | Klett | 128/234 |
| 1,561,986 | 11/1925 | Küppers | 128/234 |
| 3,102,082 | 8/1963 | Brewer | 195/103.5 R |
| 3,107,204 | 10/1963 | Brown et al. | 195/103.5 R |
| 3,709,791 | 1/1973 | Lichtenstein | 195/127 |
| 3,713,985 | 1/1973 | Astle | 194/103.5 R |
| 3,826,717 | 7/1974 | Gilbert et al. | 195/103.5 R |

*Primary Examiner*—Alvin E. Tanenholtz
*Assistant Examiner*—Robert J. Warden
*Attorney, Agent, or Firm*—Fred Philpitt

[57] ABSTRACT

The present invention relates to a method and device for the examination of a sample which may contain microorganisms, whereby the sample is mixed with a microorganism growth medium, and optionally an indicator, the mixture is incubated and thereafter examined for the presence of growing colonies.

8 Claims, 10 Drawing Figures

MICROORGANISM TESTING DEVICE AND METHOD

BACKGROUND

In order to analyze a sample for the presence of microorganisms (such as bacteria) it has hitherto been usual to either transfer a certain amount of the sample by a pipette to a dish, add a growth medium and either mix to distribute the bacteria or to simply distribute the bacteria on the surface of a solid growth substrate. After incubation examination is carried out to ascertain the extent of growth. In the cultivation of anaerobic microorganisms an anaerobic environment must be provided. The conventional manner of accomplishing this has been to place the dish, after distribution of the microorganisms in the growth medium (and after solidification of the growth medium, which generally comprises a nutrient broth and agar) in a closed growth vessel, where the oxygen of the air is removed (e.g. by hdyrogen gas and a catalyst which promotes the formation of water). This involves complicated and expensive techniques and equipment, and test errors can arise from mixing owing to contact with the air. Furthermore many of the microorganisms of interest are pathogenic, which means that risks for laboratory personnel may arise.

OBJECTS

The object of my invention has thus been to provide a method for the determination of the presence of microorganisms which involves a routine simple enough so that relatively untrained personnel can manage it, where complicated equipment is avoided, where the risk of infection of the laboratory personnel is reduced and where the reliability of the results is improved.

THE INVENTION GENERALLY

According to my invention a defined volume of a sample and a predetermined volume of a growth medium are sucked into a growth chamber having clear or translucent walls by means of a piston, and mixed therein, the opening to the chamber thereafter being closed if desired. Incubation is then carried out whereafter examination for growing colonies is made through the clear or translucent walls of the growth chamber. Alternatively the growth medium and then the sample can be sucked into the growth chamber and mixed therein.

It is possible to carry out the method according to my invention by using a conventional so-called non-returnable syringe with clear or translucent walls of non-toxic plastic. However, on account of the cylindrical shape of the ordinary syringe the determination of the number of colonies of organisms can sometimes be difficult. Furthermore, syringes are usually not adapted for mixing the sample with another medium or a sample with a diluant. The invention also relates to a device for carrying out the method according to the invention.

The device according to my invention is characterized in that it comprises a growth chamber with at least two clear or translucent walls spaced opposite each other and a third wall which has a suction opening for a sample and a growth medium. The chamber has an oblong cross-section wherein the greatest length of the cross-section is considerably greater than greatest width of the cross-section and preferably more than twice as great. In the device of my invention the growth chamber is also bounded by displaceable wall shaped as a piston equipped with a piston rod.

THE DRAWINGS

The invention will be described hereinafter in greater detail with reference to the accompanying drawings wherein FIG. 1 is a perspective view, partly in cross-section, of one embodiment of my invention;

FIG. 4 is a cross-sectional view of the growth chamber;

Figure 5:
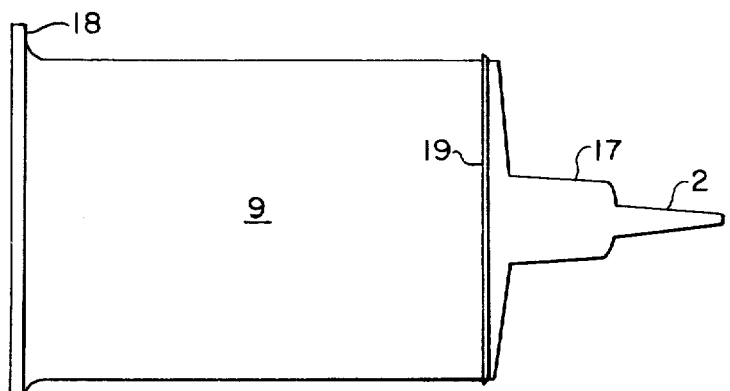
Figure 6:
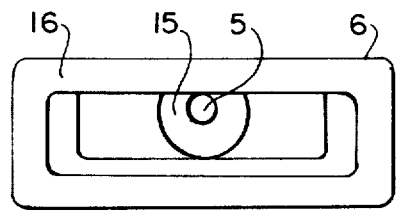

FIG. 5 a plan view of the piston member;

FIG. 6 is an interior end view of the growth chamber from the open part in order to show the interior of the chamber;

FIGS. 7-10 show an analyzing kit that can be used in connection with the method and device of my invention.

THE INVENTION IN DETAIL

Figure 1:
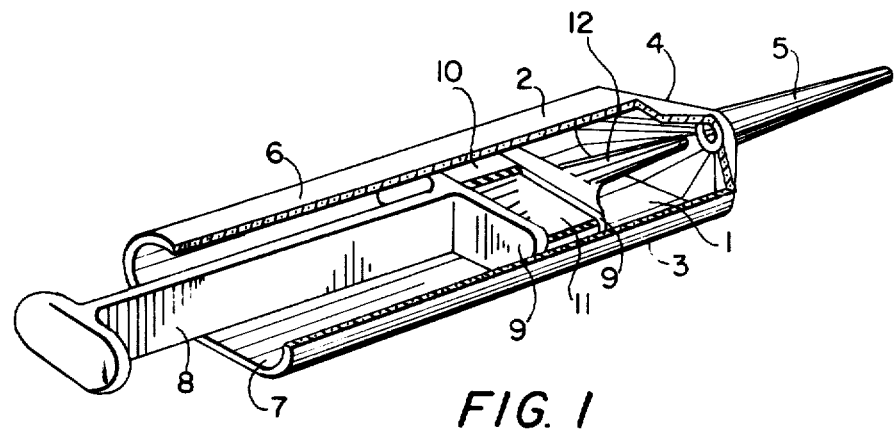
Figure 2:
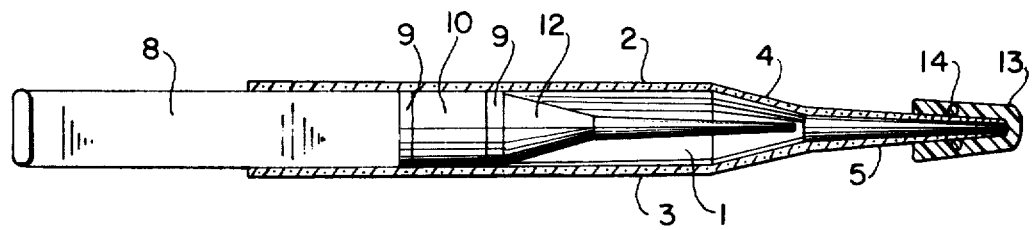
FIG. 2 is a side view in a cross-section of the device of FIG. 1 with an affixed protective cap.
Figure 3:
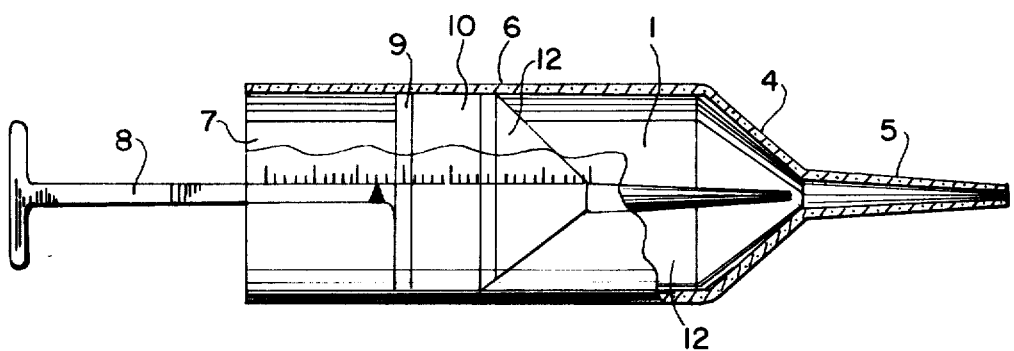
FIG. 3 is a top view, partly in cross-section of the device of FIG. 1.

Referring now to FIGS. 1-3 it will be seen that a growth chamber 1 is bounded by two clear or translucent walls 2 and 3. The third wall 4 of the growth chamber includes an inlet passageway or suction opening that includes an elongated spout 5. Walls 6 and 7 are extensions of walls 2 and 3 and are likewise clear or translucent. Growth chamber 1 also has one displaceable wall in the form of a piston member 9 that includes an axially extending piston rod 8. A sealing gasket 10 (e.g. of rubber) is provided around a groove-like section of the piston so as to insure a gas-tight seal adjacent the periphery of the piston member.

The section 12 of the piston that faces towards the spout 5 is preferably given a generally conical contour so that it will conform to the similarly contoured section 4 adjacent to the spout 5. Sections 4 and 12 are preferably made from a clear or translucent material.

To close the suction port or inlet passageway a protective cover or cap 13 can be affixed to the spout 5. An O-ring sealing 14 can be arranged in the cover or cap 13. The wall 2 preferably is provided with the volumetric graduations as is shown in FIG. 3.

Preferably the passage between the spout 5 and the interior of the chamber 1 is shaped in such manner that the angle between the inlet (the spout) and the chamber causes turbulence (and thereby good mixing) when the growth medium is sucked into the chamber 1 containing the sample.

When my device is to be used for cultivation of anaerobic bacteria the piston 9 is first moved towards the section 4 so that the section 12 nests or abuts against section 4, whereafter the spout 5 is dipped into the sample and the desired amount of sample is sucked up by moving the piston to the left. The spout 5 is thereafter dipped into melted growth substrate with agar, to which a suitable indicator may have been added, and the desired amount is sucked into the chamber 1 by continuing to move the piston 5 further to the left whereby, as has been mentioned above, the passage between the spout 5 and the inner portion of the chamber 1 is preferably shaped in any manner that will give a satisfactory mixing of the sample and the growth medium. The protective cover 13 or cap is thereafter affixed to the spout 5 in order to avoid admission of air and the device is incubated at a suitable temperature. After incubation the device is examined for growing colonies e.g. by holding the device up to the day-light or towards another source of light and the presence or abscence of colonies of organisms is looked for through the clear or translucent walls of the growth chamber.

The term "clear or translucent" walls not only means walls as clear as glass but also walls of a limited opacity which nevertheless give sufficient light transmission for the colonies of microorganisms developed during cultivation to be distinguished from their environment when examination is carried out with a source of light in the background.

With aerobic microorganisms it is not so important as with anaerobic microorganisms to use a device where the end of the piston facing towards the spout is conically contoured. With aerobic tests it is suitable to shape the end of the piston member somewhat so that an aircushion is obtained above the mixture of the sample and the growth medium in the chamber. The section 12 can be omitted for use with anaerobic microorganisms but in such a case the spout 5 should be filled with e.g. hydrogen gas or carbon dioxide. When section 12 is omitted it is possible e.g. to provide graduations on the spouts and give this an innervolume which is big enough to take up the sample, whereby a greater accuracy in dosing of the sample can be achieved.

Figure 4:
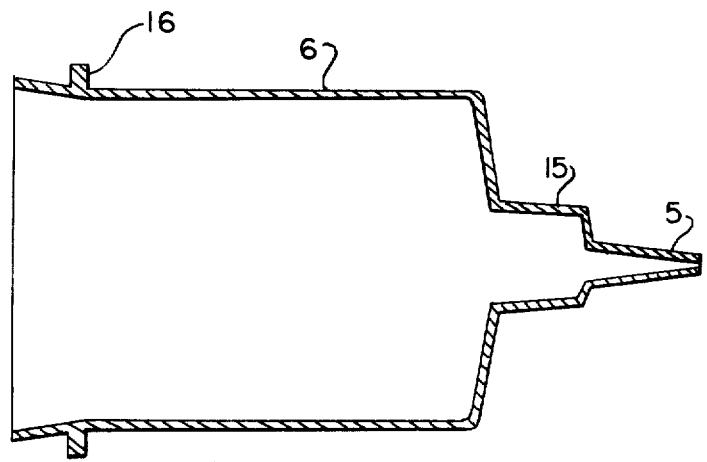
FIGS. 4-6 show a modified two-part embodiment of a device according to my invention.

In FIG. 4 the growth chamber 6 is a hollow preferably injection molded body of generally rectangular cross section and made of a transparent plastic material, e.g. polystyrene one end of which is provided with a slightly conical narrower part 15 that terminates in the spout 5. The opposite end of the chamber has a handle rib 16 on the outside of the chamber. The purpose of the narrow part 15 is to allow a more exact determination of the sample volume introduced. FIG. 5 shows the piston member 9 preferably in the form of an injection molded body having the same outer shape as the inner shape of the growth chamber 6 of FIG. 4 and provided with a narrow part 17 and an extension 2 instead of a spout 5. The other end of the piston member is provided with a handle rib 18. The piston member 9 may be made of plastic material e.g. expanded HD-polyethylene. A rib 19 is provided adjacent the top end of the member 9 which may serve a strengthening rib and/or as a sealing rib.

The narrow part 17 and the extension 2 can be omitted for aerobic tests. An air cushion will be formed over the mixture of the sample and the growth medium and the air cushion will be in communication with the open air by means of the spout 5. It is important that the mixture in the spout 5 is removed by a further stroke with the piston member 9. FIG. 6 shows that the axis of the spout 5 is placed near one of the walls. By means of this arrangement the spout after a sample and the growth medium have been sucked in a layer of air is formed over the whole upper surface of the mixture of sample and medium directly under the upper horizontal wall of the growth chamber 6.

The cross-section of the growth chamber should have a maximum width (or depth) not exceeding 20 mm, preferably 5 to 12 mm to allow a good visual analysis through the whole system. The maximum length of the cross-section can be varied within very wide limits. Generally it falls within the range of from 20 to 70 mm, preferably 25 to 50 mm. By graduating the chamber from 1 to 10 ml my device can be used for diluting the sample 1/10 before analysis. By this process pipettes are avoided.

For fast routine on the spot the device according to my invention can be supplied with growth medium (broth) already in the growth chamber, whereby the only step which has to be taken on the spot is to suck a certain amount of sample into the chamber. In such a case it can be suitable to provide the device with a locking means which can lock the piston rod in two positions corresponding to the situations when broth and a mixture of broth and sample respectively are sucked into the growth chamber.

If desired the piston rod can be provided with guiding or steering arms which bear on the walls of the chamber.

The method and the device according to my invention can be used in a great number of situations where a sample is examined for contents of microorganisms such as in medical, veterinary and bacteriological analysis. Examples are analysis of food samples, drinking water, bathing-water, etc. Another example is the evaluation of the antimicrobial effect of a substance or comparisons of such effects of two or more substances.

A third embodiment of my invention relates to an analysing kit to be used in connection with the previously described method and device. The use of the kit will improve the reliability of the results obtained by using the method and device.

In determining the presence of microorganism in a sample a certain amount of the sample is added to a growth medium, whereafter incubation and examination is carried out. It is often desirable to make such a determination for different bacteria which require different growth media. It can also be desirable to find the dilution of the sample to be tested where no growth occurs. In such cases the sample must be e.g. diluted in several sequences, and normally in the following order: 1, $1/x$, $1x^2$, $1/x^3$, etc. ($x$ usually being 10). Each dilution is made in an auxiliary medium in beakers or sterile test tubes from which samples are withdrawn at different concentrations and tested for growth in different growth media.

The analysing kit according to the present invention relates to a support comprising at least two reservoirs, each reservoir containing the same amount of auxiliary medium.

Figure 7:
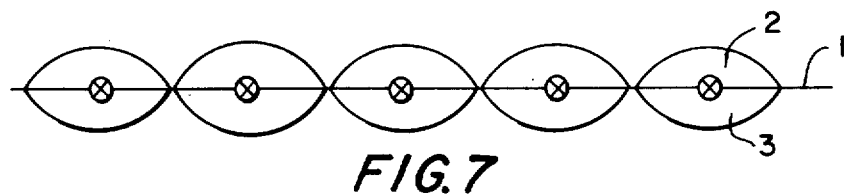
Figure 8:
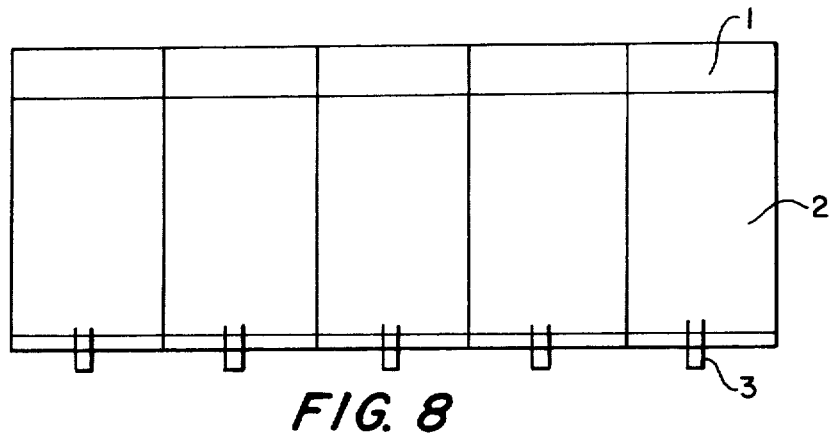
Figure 9:
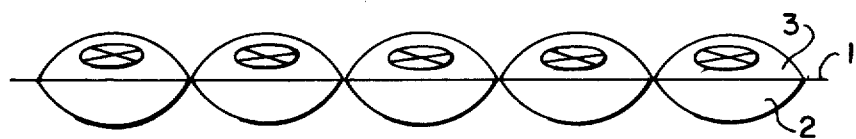
Figure 10:
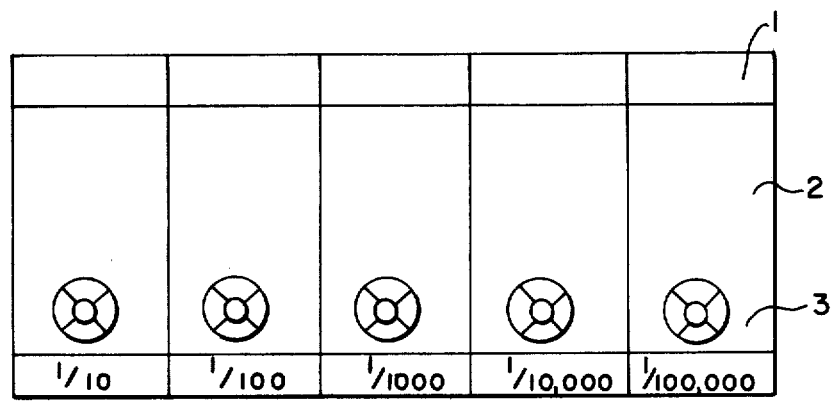

FIGS. 7 and 9 are side views of an analyzing kit where 1 is the support, 2 is a reservoir and 3 is a reclosable seal which fits the spout of the device described in FIGS. 1–6. In FIG. 7 the seals are placed in the bottom of the reservoirs. FIGS. 8 and 10 show top views of the kits of Figs. 7 and 9. There are markings on the support 1 to indicate the dilutions to be obtained.

The amount of the auxiliary medium in each reservoir is preferably 9 ml or a 10-power of this. Each reservoir should also contain a reclosable seal which fits the spout of the device according to the invention. The auxiliary medium is preferably an inert dilution medium, an inactivator or a nutrient medium. By using my analyzing kit for dilution purposes a certain amount of the sample to be tested, e.g. 1 ml, is sucked into the device, whereafter the whole amount of auxiliary medium (which in this test is a dilution medium) in the first reservoir of the analyzing kit also is sucked into the device. As the passage between the spout and the interior of the chamber in the device preferably is shaped in such a manner that turbulence is obtained a good mixing of sample and auxiliary medium is provided for. Thereafter the content of the device is injected into the empty reservoir in the kit and when this is completely filled a ten-fold dilution of the sample is obtained. As the reservoir only contains 9 ml the device still contains 1 ml of a ten-fold dilution of the sample. By repeating the same procedure but using the 9 ml of dilution medium in the second reservoir, sucking this into the device containing 1 ml of diluted sample and injecting 9 ml of this mixture, now diluted 100 times, into the empty reservoir, mixing the remaining 1 ml in the device with the dilution medium in the third reservoir etc. dilutions of the sample are obtained at 1/10, 1/100, 1/1000 etc. These dilutions are then tested for quantitative bacterial growth according to the method of the invention and in the device of the invention.

When the auxiliary medium contains an inactivator the analyzing kit is suitable for testing anti-bacterial compounds. According to one method for testing the bactericidal activity of a compound in relation to different types of bacteria, the compound and a reference in predetermined dilutions are allowed to be in contact with broth cultures each containing the bacteria. After 5 minutes 1 ml samples from each broth culture tube is sucked into devices according to the invention. The test procedure will now be described for one of the broth cultures but is understood that the same procedure is used for the other samples. Into the device is sucked 9 ml of inactivator from the first reservoir in the analyzing kit and the mixture of inactivator and sample is again injected in the reservoir and thus a 1/10 dilution is obtained. 1 mml is left in the device and the procedure is repeated two times and the following dilutions are obtained: 1/10, 1/100 and 1/1000. Into the last device containing 1 ml dilutions is sucked nutrient medium and the device is left in a heating tank for incubation. This procedure is repeated with two new devices for the dilutions 1/10 and 1/100 respectively. The inactivator stopped and further action of the anti-bacterial agent, and each live bacterium left in addition to the inactivator produces a colony in the nutrient medium in the device which is easy to count through the flat, transparent walls. The number of colonies is counted and gives the result of the test.

One great advantage of the analyzing kit according to my invention is that untrained personnel can easily handle the kit as there is no need for measuring up and portioning auxiliary medium, it is easy to handle the different dilutions as the kit can be adapted to contain just as many reservoirs as dilutions required for the test in question. According to one embodiment the kit comprising a support and reservoirs can be manufactured as a belt containing a very large number of reservoirs. In starting a test the belt is cut off to give a kit containing as many reservoirs as required for the test. Before starting the dilution procedure the dilutions can be marked by a pencil for each reservoir and when the dilutions are made there is no risk of mixing them up.

What I claim is:

1. A method for determination of the presence of microorganisms in a sample wherein said sample and a growth medium for microorganisms are each individually sucked into a non-circular growth chamber having clear or transparent walls, said sucking being accomplished through one wall of said growth chamber which has an inlet passageway, said sucking being conducted by means of a displaceable opposite wall in the growth chamber, an upper wall and a lower wall of the growth chamber being spaced apart and disposed in a parallel relationship and connected to each other with side walls, the chamber having a cross section wherein the length of the cross section is more than two times greater than the width of the cross section, mixing said sample and growth medium in the growth chamber, incubating to permit growth of the microorganisms and examining the inoculated chamber through the clear or transparent walls of said growth chamber for the presence of growing colonies.

2. A device for collecting and growing microorganism which includes:
   a. an elongated chamber,
   b. an inlet passageway located at one end of said chamber which is adapted to accomodate the passage of both a sample and a growth medium into said chamber,
   c. a piston member forming one movable wall in said chamber, the movement of said piston member from one position to another in said chamber being perpendicular to the cross-section of said chamber, creating a suction force upon said inlet passageway to thereby draw sample and growth medium into said chamber, said elongated chamber having a non-circular cross-section and comprising
   1. an upper wall and a lower wall that are spaced apart and disposed in a parallel relationship,
   2. two side walls that are spaced apart, each of said side walls extending between opposed edges of said an upper and lower walls,
   3. the chamber having a cross section wherein the length of the cross section is more than two times greater than the width of the cross section.

3. A device according to claim 2 characterized in that said inlet passageway is elongated to a spout.

4. A device according to claim 3 characterized in that the end of the piston member facing the inlet passageway has a generally conical contour that closely approximates the generally conical contour of said inlet passageway.

5. A device according to claim 4 characterized in that the area between the inlet passageway and the interior of said chamber is shaped in such a manner that turbulence will be created when sucking the sample and the growth medium into the chamber.

6. Device according to claim 4 characterized in that the spout is provided with volumetric graduations and has an inner volume sufficiently large for taking up the sample.

7. A device according to claim 3 characterized in that it also includes a protective cover or cap which is intended to be affixed over the end of said spout.

8. A device according to claim 2 characterized in that at least one of the walls of the chamber is provided with volumetric graduations.

* * * * *